(12) United States Patent
Chang et al.

(10) Patent No.: US 8,702,009 B2
(45) Date of Patent: Apr. 22, 2014

(54) BIOCHIP MEASURING SYSTEM AND BIOCHIP MEASURING APPARATUS AND BIOCHIP AND STAMP MARKING AND IDENTIFICATION METHOD

(75) Inventors: Yao-Tsung Chang, New Taipei (TW); Chia-Hsien Li, New Taipei (TW); Ting-Wen Liu, New Taipei (TW); Pai-Yang Lin, New Taipei (TW)

(73) Assignee: Wistron Corporation, Hsichih, New Taipei (TW)

( * ) Notice: Subject to any disclaimer, the term of this patent is extended or adjusted under 35 U.S.C. 154(b) by 0 days.

(21) Appl. No.: 13/597,269

(22) Filed: Aug. 29, 2012

(65) Prior Publication Data

US 2013/0200141 A1    Aug. 8, 2013

(30) Foreign Application Priority Data

Feb. 4, 2012    (TW) .............................. 101103653 A (51) Int. Cl.
*G06K 19/06*    (2006.01)
(52) U.S. Cl.
USPC ........................................................ 235/494
(58) Field of Classification Search
USPC ........................................... 235/494, 462.01
See application file for complete search history.

(56) References Cited

U.S. PATENT DOCUMENTS

| 2005/0284773 | A1* | 12/2005 | Allen .......................... 205/777.5 |
| 2006/0035247 | A1* | 2/2006 | Ko et al. ............................. 435/6 |
| 2010/0105074 | A1* | 4/2010 | Covey et al. .................... 435/7.1 |
| 2010/0312574 | A1* | 12/2010 | Yoo ................................... 705/2 |

FOREIGN PATENT DOCUMENTS

CN    102308197 A    1/2012

OTHER PUBLICATIONS

Office action mailed on Nov. 12, 2013 for the China application No. 201210053516.3, p. 3-9.

* cited by examiner

*Primary Examiner* — Christle Marshall
(74) *Attorney, Agent, or Firm* — Winston Hsu; Scott Margo (57) ABSTRACT

The present invention discloses a biochip measuring system. The cytometer system includes a biochip and a biochip measuring apparatus. The biochip includes a substrate, for carrying bio-molecule droplet, and a stamp marking area, for receiving or displaying a stamp for identifying whether the biochip is used. The biochip measuring apparatus includes a controller, a driver circuit, a driver interface, a light, a light detector, and a stamp marking unit, for marking the stamp on the stamp marking area of the biochip after the biochip measuring apparatus completes measurement of the biochip.

45 Claims, 11 Drawing Sheets

BIOCHIP MEASURING SYSTEM AND BIOCHIP MEASURING APPARATUS AND BIOCHIP AND STAMP MARKING AND IDENTIFICATION METHOD

BACKGROUND OF THE INVENTION

1. Field of the Invention

The present invention relates to a biochip measuring system and biochip measuring apparatus and biochip and stamp marking and identification method, and more particularly, to a biochip measuring system and biochip measuring apparatus and biochip and stamp marking and identification method capable of determining whether a biochip is used by identifying and marking a stamp of the biochip.

2. Description of the Prior Art

A specific (or colored) molecule emits a fluorescent light after a light in a cytometer beams a specific light to the molecule of flow droplet, such that the fluorescent light can be detected by utilizing a light detector. Each suspend particle scatters the light when passing through a beam, and fluorescent chemicals in the each suspend particle are excited and emitting the fluorescent light having a frequency lower than the light as well. The combination data of a scattered light and the fluorescent light is recorded by detectors, and physical and chemical properties of each particle can be derived according to fluctuations (each cell may display a peak of the scattered light or the fluorescent light) in brightness of each detector.

Figure 1:
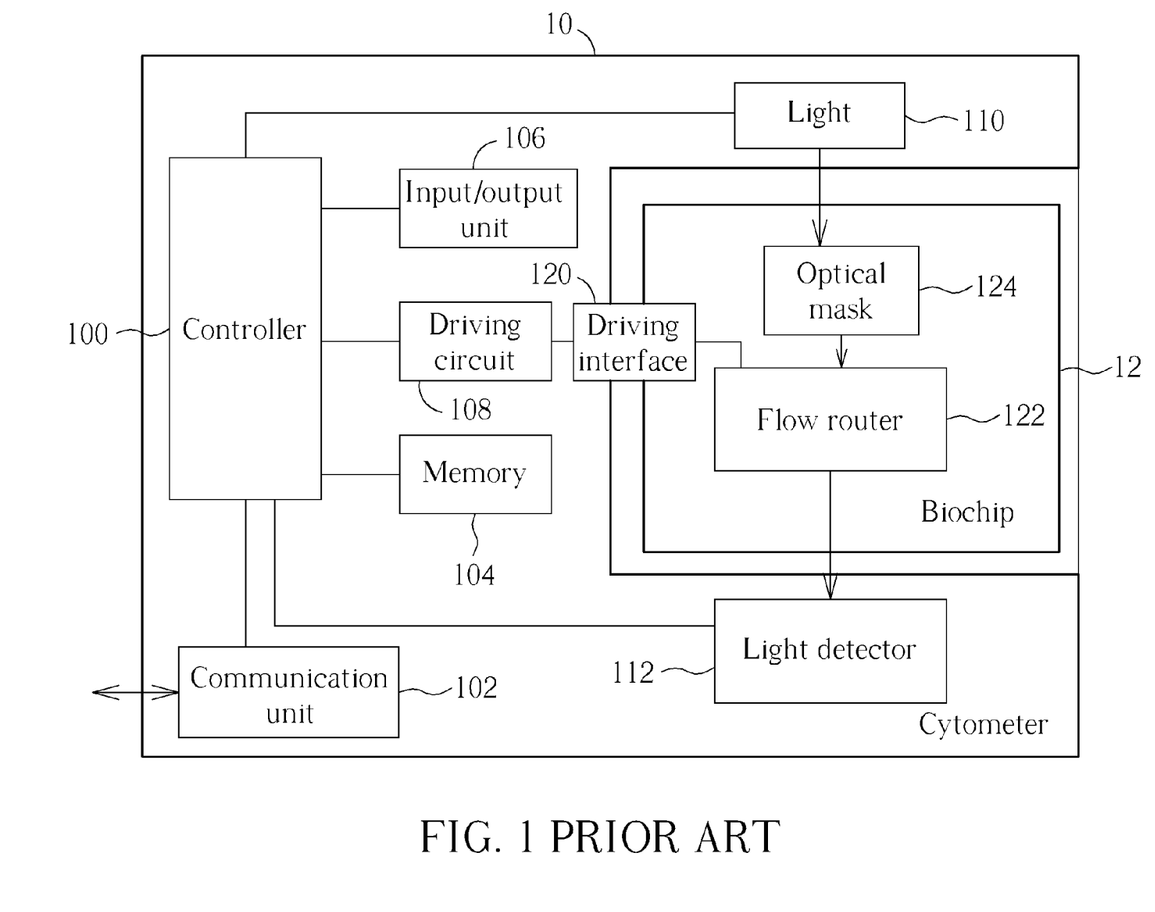
FIG. 1 is a schematic diagram of a cytometer in the prior art.

For example, please refer to FIG. 1, which is a schematic diagram of a cytometer 10 in the prior art. As shown in FIG. 1, in order to facilitate preparation before measurement, a placement of droplets to be measured and a droplet moving path are further manufactured in a biochip 12. In the cytometer 10 and the biochip 12, a controller 100 can communicate with a host via a communication unit 102, store the data in a memory 104 or execute a program code stored by the memory 104, execute a command received by an input/output unit 106, control the droplets to be measured in a flow router 122 to flow through a specific path through a driving interface 120 via a driving circuit 108, and control a light 110 to beam the light on the droplets to be measured through an optical mask 124 for reducing optical noise, such that a light detector 112 can generate a detecting result for the controller 100, to perform following actions. The related operations of the conventional cytometer 10 and the biochip 12 are known to those skilled in the art, and are not narrated hereinafter.

However, if the used biochip 12 is not completely cleaned up and is reused again, the biochip 12 may have a residual pollution, such that a measuring result is wrong. The conventional cytometer 10 does not identify used recording of the biochip 12 when the cytometer 10 and the biochip 12 are combined to perform measurements. Thus, there is a need for improvement of the prior art.

SUMMARY OF THE INVENTION

It is therefore an objective of the present invention to provide a biochip measuring system and biochip measuring apparatus and biochip and stamp marking and identification method capable of marking and identifying a stamp, to determine whether a biochip is used.

The present invention discloses a biochip measuring system. The biochip measuring system includes a biochip and a biochip measuring apparatus. The biochip includes a substrate, for carrying bio-molecule droplet; and a stamp marking area, for receiving or displaying a stamp for identifying whether the biochip is used. The biochip measuring apparatus includes a controller; a driver circuit, electrically connected to the controller; a driver interface, electrically connected to the driver circuit, and contacting with the biochip be measured; a light, electrically connected to the controller, for timely providing a measuring light to the biochip; a light detector, electrically connected to the controller, for detecting a light reaction after the light irradiates the biochip and generating a measuring result; and a stamp marking unit, for marking the stamp on the stamp marking area of the biochip after the biochip measuring apparatus completes measurement of the biochip.

The present invention further discloses a biochip measuring apparatus, for measuring a biochip. The biochip measuring apparatus includes a controller; a driver circuit, electrically connected to the controller; a driver interface, electrically connected to the driver circuit, and contacting with the biochip be measured; a light, electrically connected to the controller, for timely providing a measuring light to the biochip; a light detector, electrically connected to the controller, for detecting a light reaction after the light irradiates the biochip and generating a measuring result; and a stamp marking unit, for marking the stamp on the stamp marking area of the biochip after the biochip measuring apparatus completes measurement of the biochip.

The present invention further discloses a biochip. The biochip includes a substrate, for carrying bio-molecule droplet; and a stamp marking area, located on the substrate, for receiving or displaying a stamp for identifying whether the biochip is used; wherein, a biochip measuring apparatus marks the stamp on the stamp marking area of the biochip after completes measurement of the biochip.

The present invention further discloses a stamp marking and identification method, for a biochip measuring apparatus. The stamp marking and identification method includes identifying whether a stamp is on a stamp marking area of a biochip, to decide whether the biochip measuring apparatus measures the biochip.

These and other objectives of the present invention will no doubt become obvious to those of ordinary skill in the art after reading the following detailed description of the preferred embodiment that is illustrated in the various figures and drawings.

DETAILED DESCRIPTION

Figure 2:
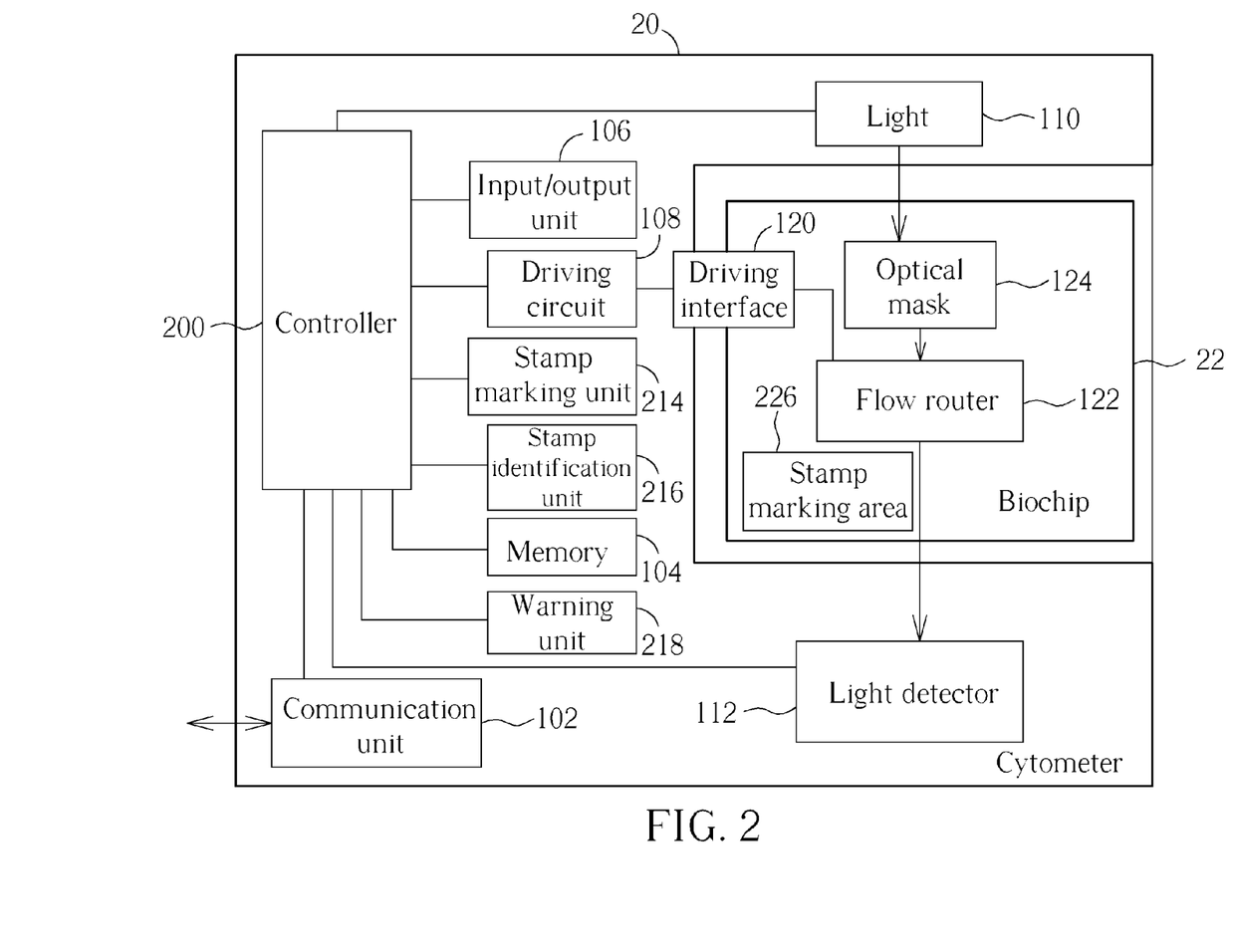
FIG. 2 is a schematic diagram of a biochip measuring system according to an embodiment of the present invention.

Please refer to FIG. 2, which is a schematic diagram of a biochip measuring system according to an embodiment of the present invention. The biochip measuring system includes a biochip measuring apparatus and a biochip 22. The biochip measuring apparatus is preferably a cytometer 20, but is not limited to this. The cytometer 20 and the biochip 22 are similar to those of the conventional cytometer 10 and the biochip 12 described in the prior art, and thus the elements with the same functionality are denoted by the same symbols, and operations of the cytometer 20 and the biochip 22 can be derived by referring to the above descriptions. The main difference between the cytometer 20 and the biochip 22 of the present invention and the conventional cytometer 10 and the biochip 12 is that the biochip 22 further includes a stamp marking area 226, which is located on a substrate for carrying bio-molecule droplet of the biochip 22, and is utilized for receiving or displaying a stamp message for identifying whether the biochip 22 is used; and the cytometer 20 further includes a stamp identification unit 216 and a stamp marking unit 214, wherein the stamp identification unit 216 can identify whether a stamp ST is on the stamp marking area 226 of the biochip 22, to decide whether the cytometer 20 measures the biochip 22, and the stamp marking unit 214 can mark the stamp ST on the stamp marking area 226 of the biochip 22 after the cytometer 20 completes measurement of the biochip 22; and in addition to performing related operations of the conventional controller 100, a controller 200 also includes controlling related operations of the stamp marking unit 214 and the stamp identification unit 216.

In such a condition, when the stamp identification unit 216 detects the stamp ST is on the stamp marking area 226 of the biochip 22 (i.e. the biochip 22 is used), the cytometer 20 does not measure the biochip 22, and make or display an error warning message by a warning unit 218. For example, the cytometer 20 can display a text or an icon message indicating the biochip is already used on a monitor, or make a specific sound via a buzzer or a voice message indicating the biochip is already used via a speaker, to provide warning, which are not limited to these, as long as the error warning message are perceived by operators. When the stamp identification unit 216 detects the stamp ST is not on the stamp marking area 226 of the biochip 22 (i.e. the biochip 22 is not used), the cytometer 20 measures the biochip 22 normally, and the stamp marking unit 214 marks the stamp ST on the biochip 22 after the cytometer 20 completes the measurement of the biochip 22. As a result, the cytometer 20 can determine whether the biochip 22 is used by identifying the stamp ST on the biochip 22, and mark the stamp ST on the biochip 22 after the cytometer 20 completes the measurement, to avoid reusing the biochip 22.

Figure 3:
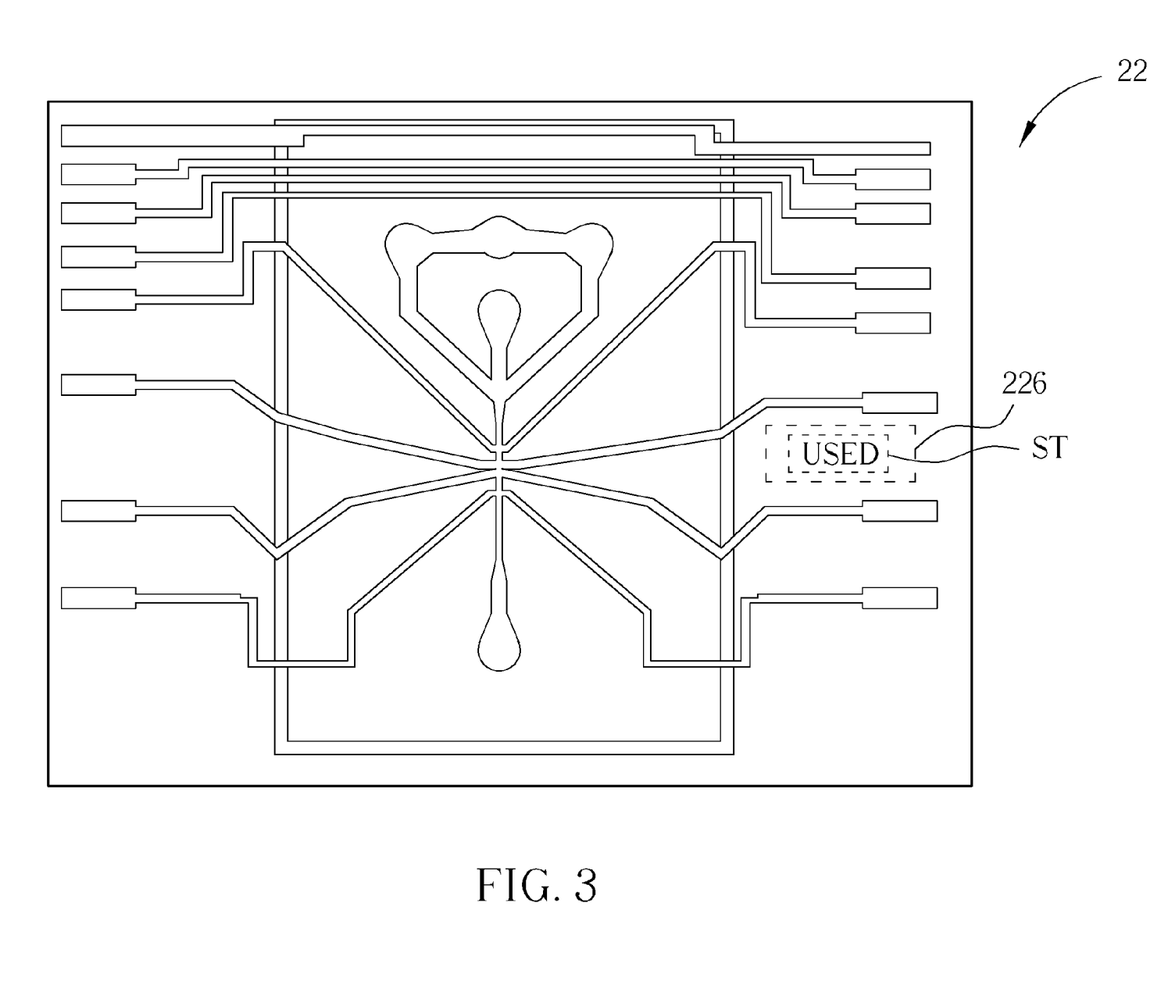
FIG. 3 to FIG. 10 are schematic diagrams of marking a stamp on a stamp marking area of a biochip shown in FIG. 2 according to different embodiments of the present invention.
Figure 4:
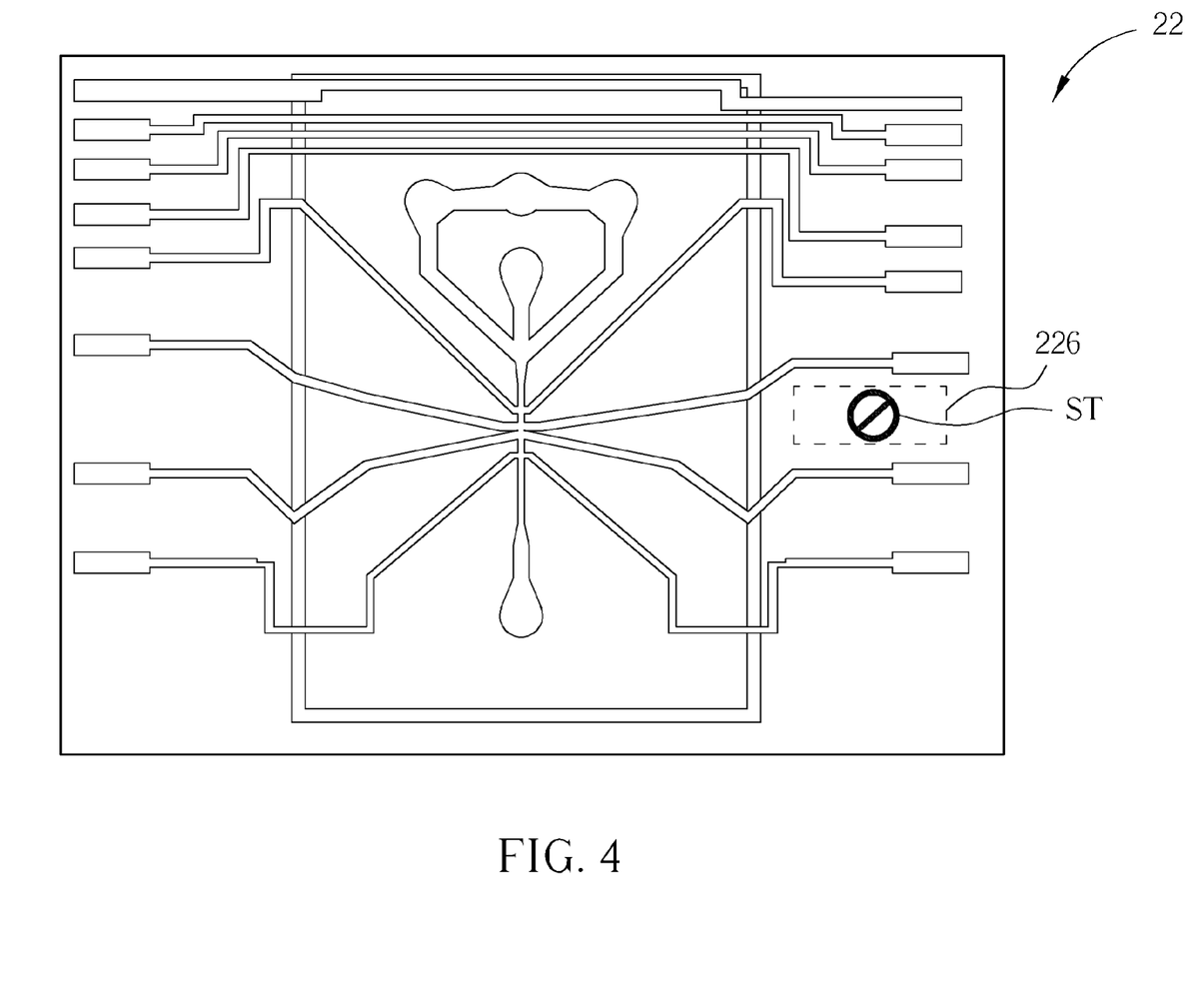
Figure 5:
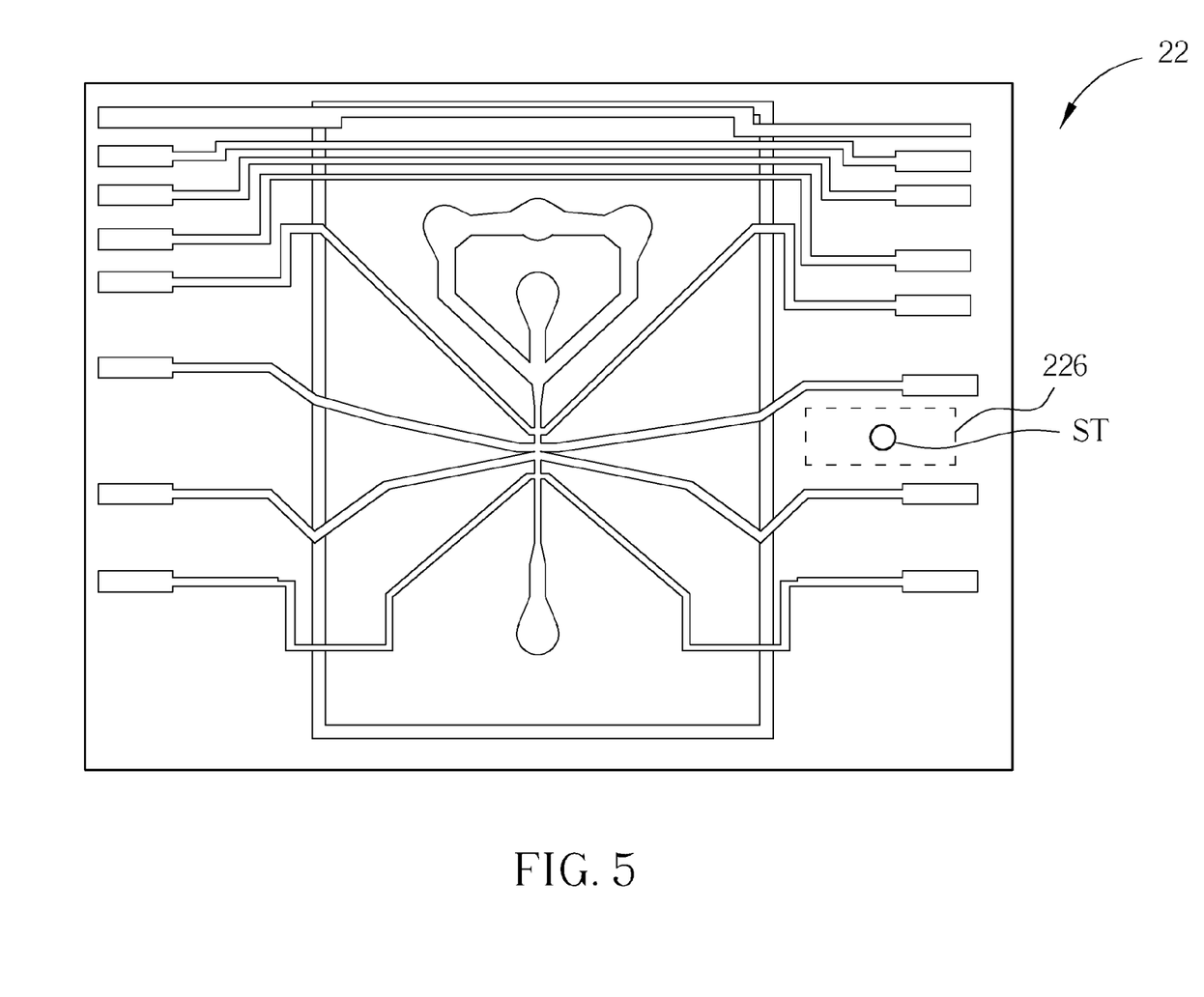
Figure 6:
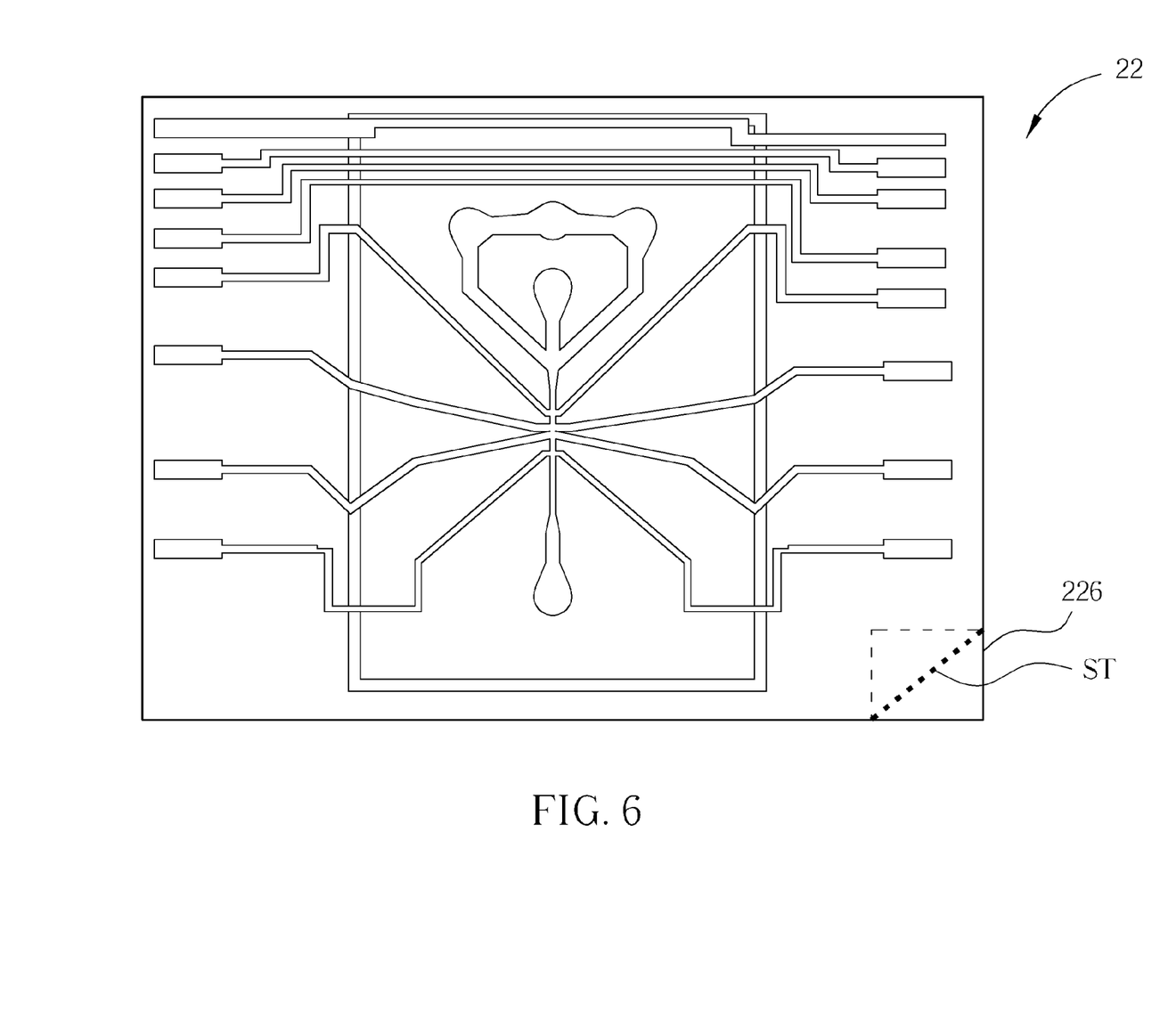

Specifically, please refer to FIG. 3 to FIG. 10, which are schematic diagrams of marking the stamp ST on the stamp marking area 226 of the biochip 22 shown in FIG. 2 according to different embodiments of the present invention. In a first embodiment, as shown in FIG. 3 and FIG. 4, the stamp marking unit 214 can mark the stamp ST with a surface processing, such as the stamp marking unit 214 can mark the stamp ST on a surface of the stamp marking area 226 of the biochip 22 with an ink coating, a printing or an optical manner (e.g. a laser etching), e.g. the stamp ST can be a text pattern (e.g. "USED" text of FIG. 3) or an icon pattern (e.g. a prohibition icon of FIG. 4). In a second embodiment, as shown in FIG. 5 and FIG. 6, the stamp marking unit 214 can mark the stamp ST with a mechanical destroying manner, e.g. the stamp ST can be a hole drilling pattern (e.g. FIG. 5) or an edge cutting pattern (e.g. FIG. 6), wherein a position that the hole drilling or the edge cutting locates is the stamp marking area 226. In the above condition, a user can identify the stamp ST (the text, the icon, the hole drilling or the edge cutting) by human eyes, to decide whether the biochip 22 is used, and the stamp identification unit 216 can also include an image capturing device (e.g. a CCD camera), for identifying the stamp ST, such that when the user puts in the biochip 22 having the stamp ST, if the cytometer 20 confirms the stamp ST is on the biochip 22 after identifying the image captured by the image capturing device, the cytometer 20 does not perform measurement to the biochip 22 already used, and makes or displays the warning message. As a result, the embodiment can prevent the cytometer 20 from re-measuring the biochip 22.

Figure 7:
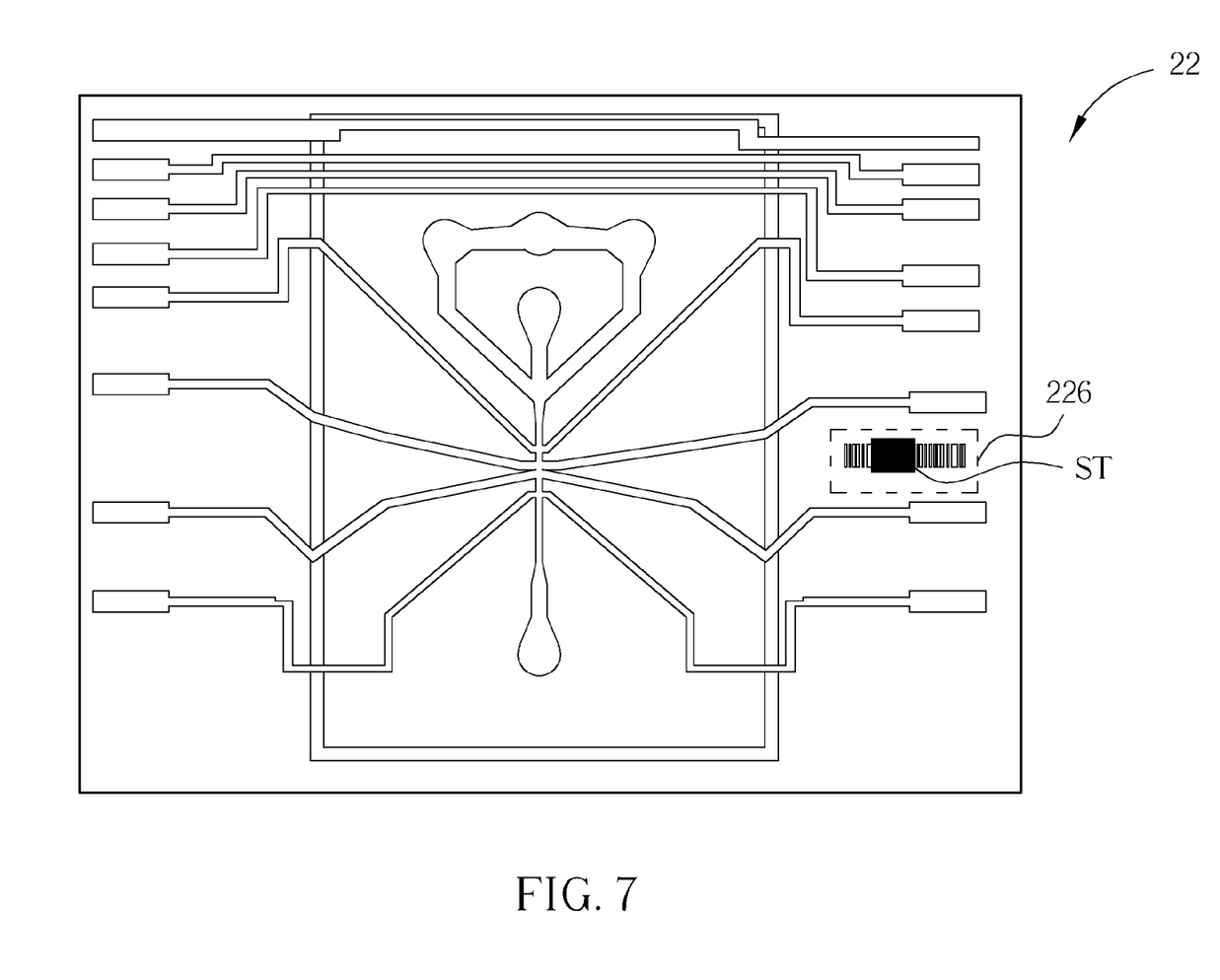

In a third embodiment, as shown in FIG. 7, the stamp marking unit 214 can mark the stamp ST by destroying, damaging or surface staining a chip measuring identification element in the biochip 22, wherein a position that the chip measuring identification element locates is the stamp marking area 226. The chip measuring identification element can be a one-dimensional or two-dimensional bar code, and the stamp ST can be generated by destroying or staining the bar code with the ink coating, the printing or the laser etching, etc. In such a condition, the user can identify the stamp ST (the bar code already destroyed) by the human eyes, to decide whether the biochip 22 is used, and the stamp identification unit 216 can also include a bar code reader, for reading the bar code to identify the stamp ST, such that when the user puts in the biochip 22 having the stamp ST, the cytometer 20 does not perform measurement to the biochip 22 already used due to a data of the bar code cannot be read correctly, and make or display the warning message. As a result, the embodiment can prevent the cytometer 20 from re-measuring the biochip 22.

Figure 8:
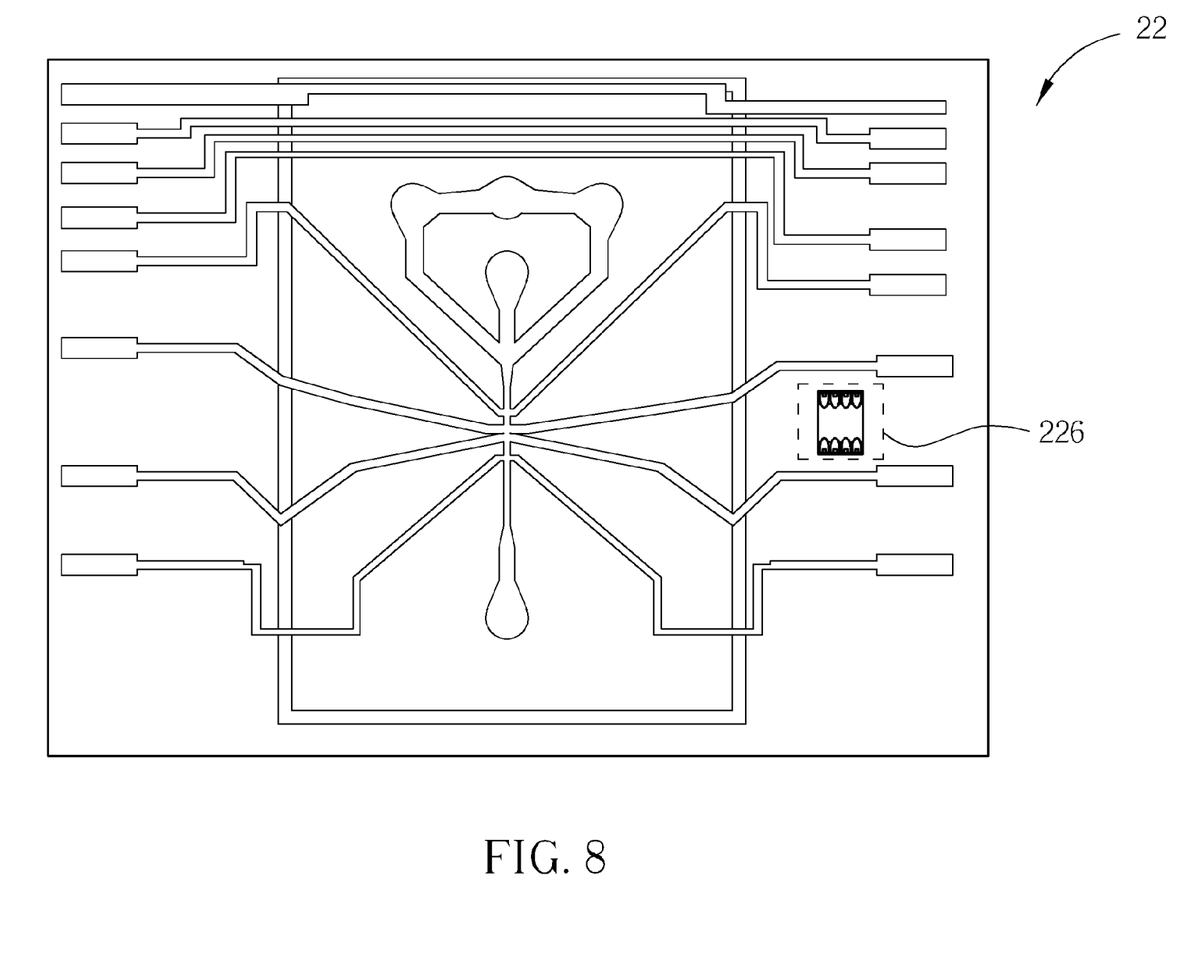

In a fourth embodiment, as shown in FIG. 8, the stamp marking unit 214 can mark the stamp ST with a memory device, e.g. the stamp marking area 226 of the biochip 22 can include a radio-frequency identification (RFID) tag or an electrically erasable programmable read-only memory (EEPROM), and the stamp marking unit 214 can write a flag into the RFID tag or the EEPROM, to mark the stamp ST (e.g. the flag set as "1" represents the stamp ST indicating the biochip 22 is used, and the flag set as "0" represents the stamp ST indicating the biochip 22 is not used). In such a condition, the stamp identification unit 216 can include a RFID tag reader or the EEPROM reader, for reading the flag to identify the stamp ST (determine whether the flag is set as 1), such that the cytometer 20 does not perform measurement to the biochip 22 already used. As a result, the embodiment can prevent the cytometer 20 from re-measuring the biochip 22.

Figure 9:
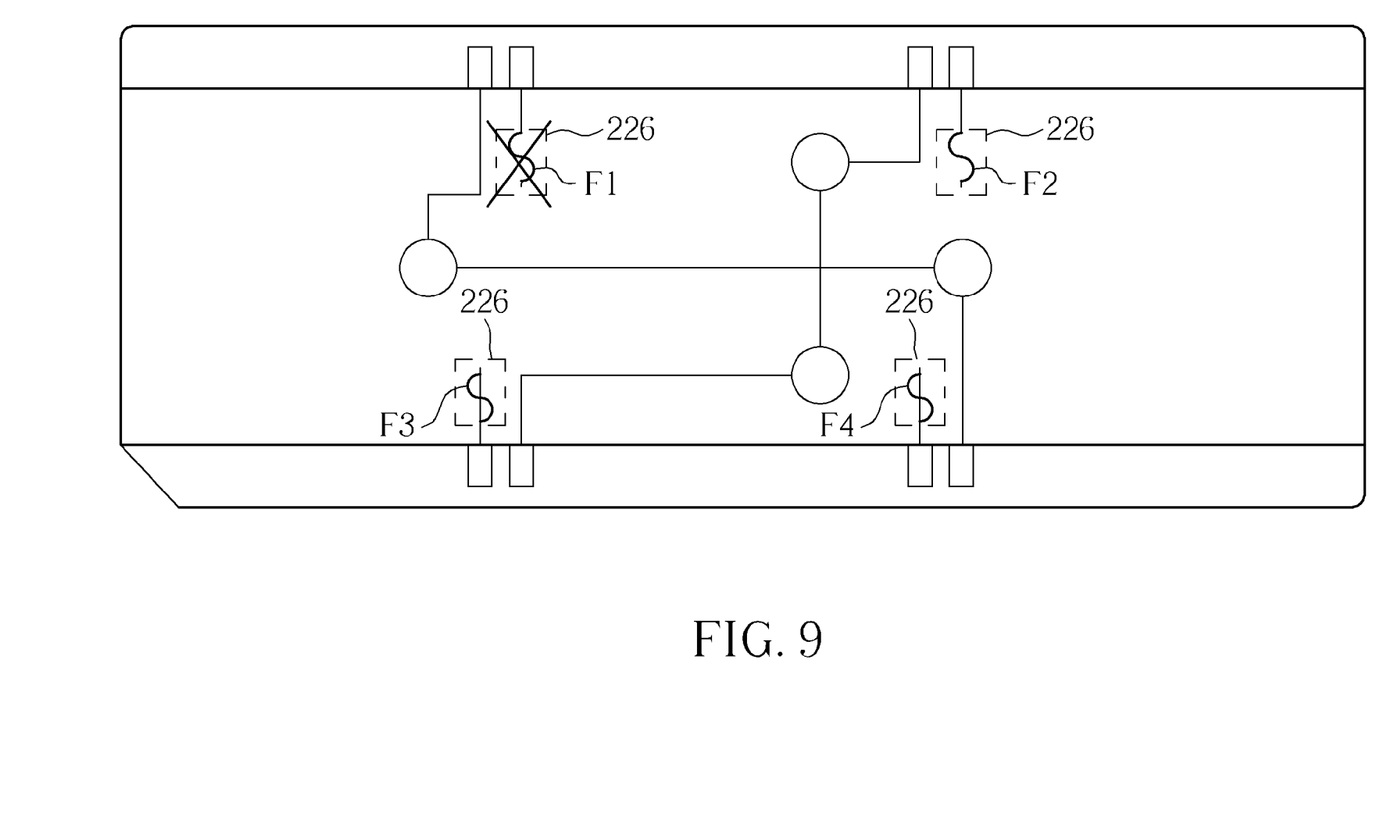

In a fifth embodiment, as shown in FIG. 9, the stamp marking unit 214 can mark the stamp ST with at least one electrical switch, e.g. the stamp marking area 226 of the biochip 22 can include fuses F1-F4, and the stamp marking unit 214 burns one of or a plurality of or all the fuses F1-F4 in the stamp marking area 226 with a large current to generate a part of or all open circuit, to mark the stamp ST (e.g. burning all the fuses F1-F4 after completely completing measurement), wherein each of the fuses F1-F4 is a narrow trace. In detail, the cytometer 20 does not completely complete measurement at one measurement, and the stamp marking unit 214 can burn one of the fuses F2-F3 not connected to a main flow path first after this measurement, to indicate the biochip 22 has been measured once, and burn all the fuses F1-F4 after completely completing the measurement of the biochip 22, i.e. the stamp ST relates that all the fuses F1-F4 are burn. In such a condition, although the user can identify the stamp ST by the human eyes, to decide whether the biochip 22 is used, the stamp identification unit 216 can also include a detecting circuit, for detecting the fuses F1-F4 to identify the stamp ST and a measurement status of the biochip 22 (e.g. detecting open and conducting statuses of the fuses F1-F4), such that the cytometer 20 can learn that the current measurement status of the biochip 22, and does not perform measurement to the biochip 22 already measured, and make or display the warning message. Noticeably, since the fuses F1-F4 are narrow traces, the fuses F1-F4 can be set by increasing layout in a circuit when the biochip 22 is made, and the fuses F1-F4 can be burnt by a power supply of the cytometer 20 directly. Therefore, it only needs to add the simple detecting circuit for detecting the open and conducting statuses of the fuses F1-F4 to realize the stamp ST with the fuses as the electrical switch increases without increasing another device and a related module (e.g. the image capturing device or all kinds of writing and reading devices). As a result, the embodiment can simply and effectively prevent the cytometer 20 from re-measuring the biochip 22.

Figure 10:
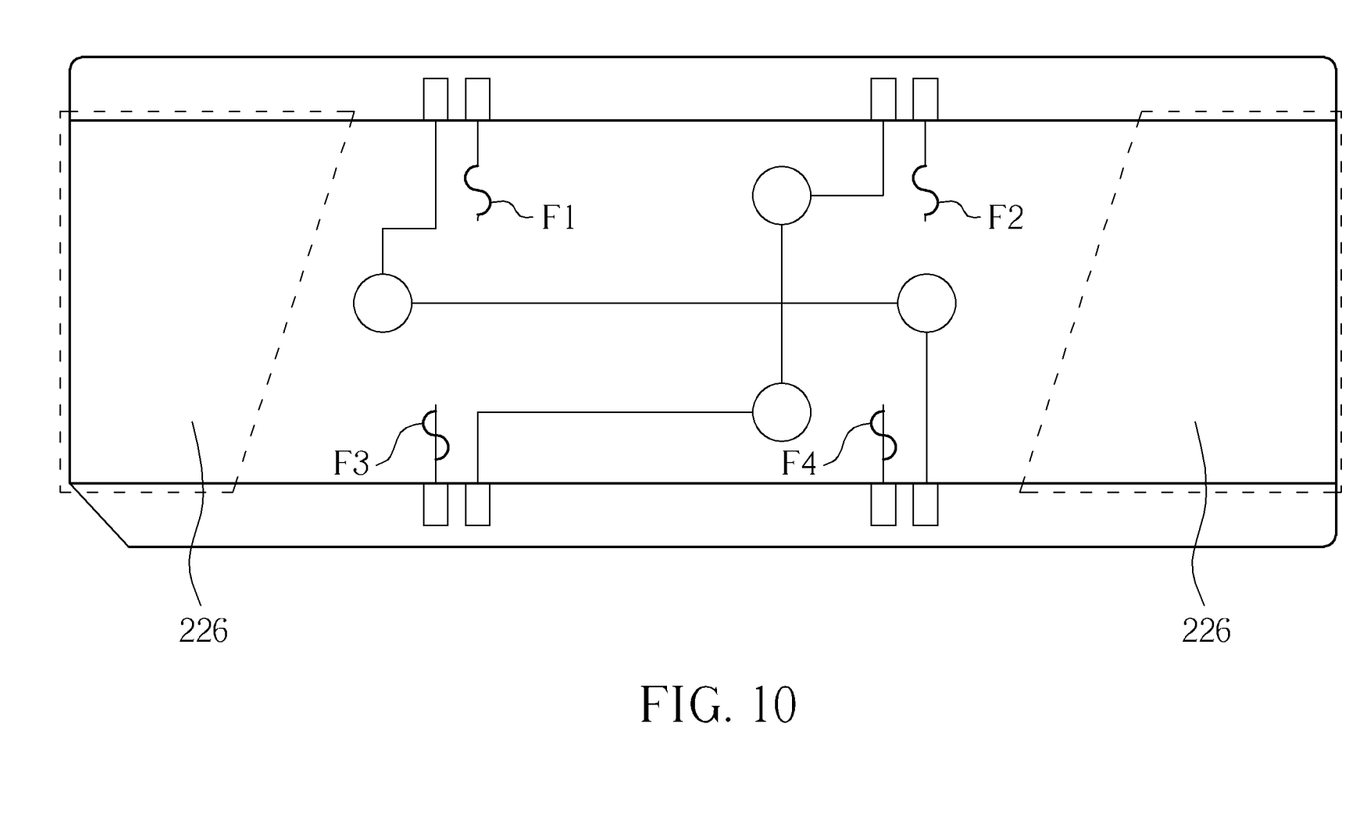

In a sixth embodiment, as shown in FIG. 10, the stamp marking unit 214 can mark the stamp ST with a color-changing of a color-changing material, e.g. the stamp marking area 226 has a color-changing chemical (e.g. a ferrous ion or a potassium dichromate prone to an oxidation reduction reaction), and the color-changing chemical can change to a specific color due to oxidation or humidity variations, to mark the stamp ST. For example, the color-changing chemical in the stamp marking area 226 initially isolated from an air by sticking an adhesive tape onto the stamp marking area 226 with the color-changing chemical, and the adhesive tape is torn from the stamp marking area 226 with the color-changing chemical after the cytometer 20 completes the measurement of the biochip 22, such that the color-changing chemical contacts with the air, and the color-changing chemical changes to the specific color due to the oxidation or humidity variations at this moment. The color-changing material can change color by the above chemical reactions, e.g. oxidation or humidity variations, and can also reach a color-changing effect of reactions of an electrical energy, a light energy, or a thermal energy. As known by those skilled in the art, the color-changing effect of reactions of the electrical energy, the light energy, or the thermal energy can be achieved by inputting voltage, illuminating light, or heating, respectively. In such a condition, although the user can identify the stamp ST by the human eyes (the specific color changed by the color-changing material), to decide whether the biochip 22 is used, the stamp identification unit 216 can also include a color detector, for detecting the specific color to identify the stamp ST (e.g. detecting a color and a wavelength of a light wave of the specific color), such that when the user puts in the biochip 22 having the stamp ST, the cytometer 20 does not perform measurement to the biochip 22 already used, and make or display the warning message. As a result, the embodiment can prevent the cytometer 20 from re-measuring the biochip 22.

Noticeably, the main spirit of the present invention is that the cytometer 20 can determine whether the biochip 22 is used by identifying the stamp ST on the biochip 22, and mark the stamp ST on the biochip 22 after completing the measurement of the biochip 22, to avoid reusing the biochip 22. Those skilled in the art may make alterations or modifications accordingly. For example, the above embodiments mark the stamp ST with implementations of the ink coating, the printing, the optical etching, the mechanical destroying, the bar code destroying, the memory device, the electrical conduction and the color-changing, but the present invention is not limited to the above implementations, as long as the stamp ST can be marked on the biochip 22 and can be identified. The present invention is also not limited to have the corresponding specific stamp identification unit 216 and can be determined with human eyes. However, in order to avoid error determination or increase automatically measurement and perform recording, the preferred method of performing automatically identifying and warning is to apply the different corresponding stamp identification units 216 according to different methods for marking the stamp ST.

Figure 11:
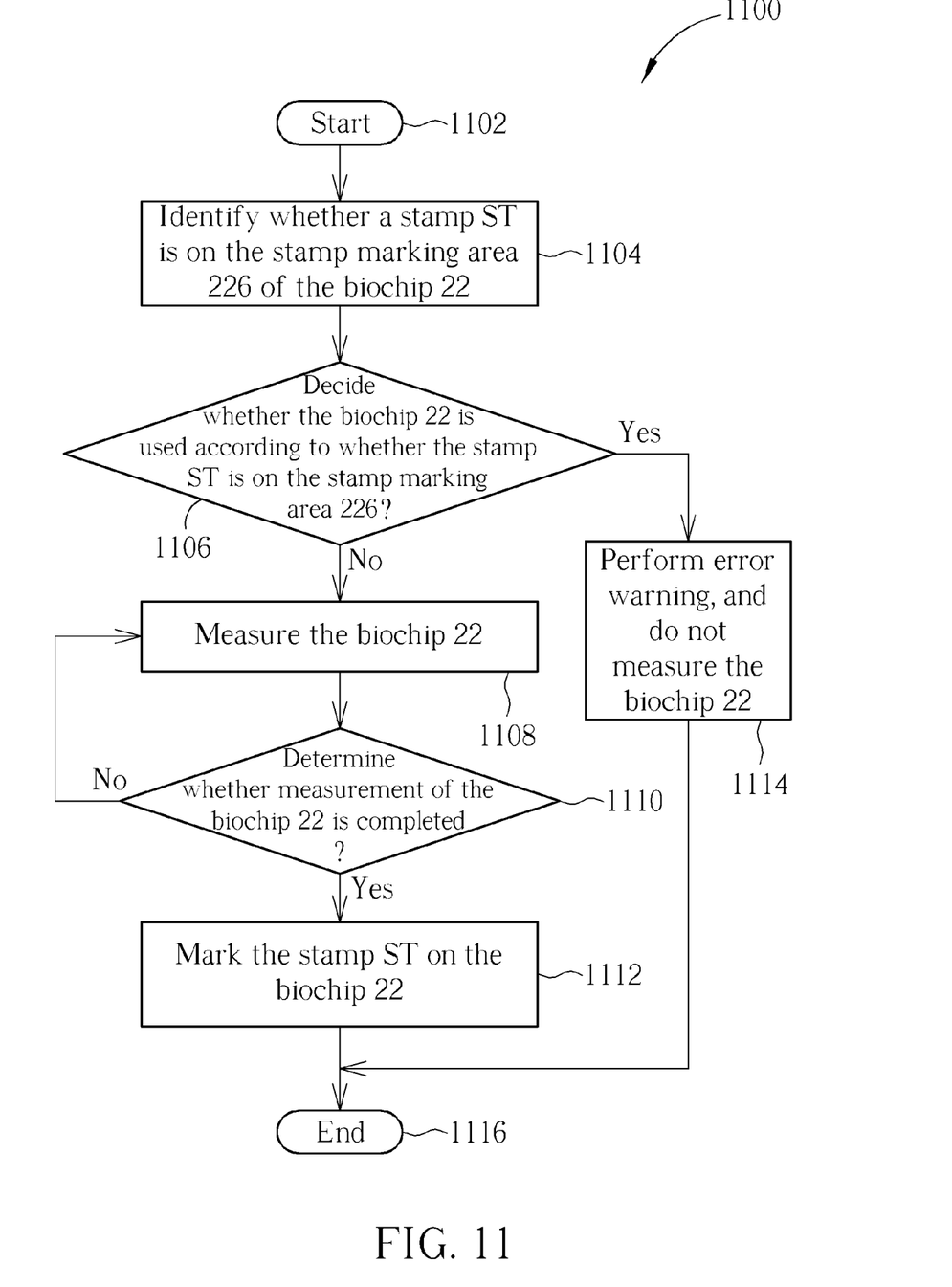
FIG. 11 is a schematic diagram of a stamp marking and identification process according to an embodiment of the present invention.

Operations of the cytometer 20 can be summarized into a stamp marking and identification process 1100 as shown in FIG. 11. The stamp marking and identification process 1100 includes following steps:

Step 1102: Start.

Step 1104: Identify whether a stamp ST is on the stamp marking area 226 of the biochip 22.

Step 1106: Decide whether the biochip 22 is used according to whether the stamp ST is on the stamp marking area 226. If yes, go to step 1114; otherwise, go to step 1108.

Step 1108: Measure the biochip 22.

Step 1110: Determine whether measurement of the biochip 22 is completed. If yes, go to step 1112; otherwise, go to step 1108.

Step 1112: Mark the stamp ST on the biochip 22.

Step 1114: Perform error warning, and do not measure the biochip 22.

Step 1116: End.

The detailed operations of the stamp marking and identification process 1100 can be derived by referring to the above descriptions. Besides, the actions of identifying and marking the stamp ST in the stamp marking and identification process 1100 can be performed with any implementation of the above embodiments, and the detailed operations can be derived by referring to the above descriptions, and are not narrated hereinafter.

In the prior art, if the used biochip 12 which is not completely cleaned up and is reused again, the biochip 12 may have a residual pollution, such that a measuring result is wrong. The conventional cytometer 10 does not identify used recording of the biochip 12 when the cytometer 10 and the biochip 12 are combined to perform measurements. In comparison, the cytometer 20 of the present invention can determine whether the biochip 22 is used by identifying the stamp ST on the biochip 22, and mark the stamp ST on the biochip 22 after completing the measurement of the biochip 22, to avoid reusing the biochip 22.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A biochip measuring system, comprising:
   a biochip, comprising:
      a substrate, for carrying bio-molecule droplet; and
      a stamp marking area, for receiving or displaying a stamp for identifying whether the biochip is used; and
   a biochip measuring apparatus, comprising:
      a controller;
      a driver circuit, electrically connected to the controller;
      a driver interface, electrically connected to the driver circuit, and contacting with the biochip be measured;
      a light, electrically connected to the controller, for timely providing a measuring light to the biochip;
      a light detector, electrically connected to the controller, for detecting a light reaction after the light irradiates the biochip and generating a measuring result; and
      a stamp marking unit, for marking the stamp on the stamp marking area of the biochip after the biochip measuring apparatus completes measurement of the biochip;
   wherein the stamp marking unit marks the stamp by adding a particular pattern for recognition with a surface processing.

2. The biochip measuring system of claim 1, wherein the biochip measuring apparatus further comprises a stamp identification unit, for identifying whether the stamp is on the stamp marking area of the biochip, to decide whether the biochip measuring apparatus measures the biochip.

3. The biochip measuring system of claim 2, wherein the biochip measuring apparatus does not measure the biochip when the stamp identification unit detects the stamp is on the stamp marking area of the biochip.

4. The biochip measuring system of claim 3, wherein the biochip measuring apparatus further comprises a warning unit, for making or displaying a warning message when the stamp identification unit detects the stamp is on the stamp marking area of the biochip and does not measure the biochip.

5. The biochip measuring system of claim 2, wherein the biochip measuring apparatus measures the biochip when the stamp identification unit detects the stamp is not on the stamp marking area of the biochip, and the stamp marking unit marks the stamp on the biochip after the biochip measuring apparatus completes measurement of the biochip.

6. The biochip measuring system of claim 1, wherein the surface processing comprises an ink coating, a printing or an optical etching.

7. The biochip measuring system of claim 6, wherein the stamp is a text pattern or an icon pattern.

8. The biochip measuring system of claim 1, wherein the biochip measuring apparatus is a flow cytometer.

9. A biochip measuring system, comprising:
a biochip, comprising:
a substrate, for carrying bio-molecule droplet; and
a stamp marking area, for receiving or displaying a stamp for identifying whether the biochip is used; and
a biochip measuring apparatus, comprising:
a controller;
a driver circuit, electrically connected to the controller;
a driver interface, electrically connected to the driver circuit, and contacting with the biochip be measured;
a light, electrically connected to the controller, for timely providing a measuring light to the biochip;
a light detector, electrically connected to the controller, for detecting a light reaction after the light irradiates the biochip and generating a measuring result; and
a stamp marking unit, for marking the stamp on the stamp marking area of the biochip after the biochip measuring apparatus completes measurement of the biochip;
wherein the stamp marking unit marks the stamp with a mechanical destroying manner.

10. The biochip measuring system of claim 9, wherein the stamp is a hole drilling pattern or an edge cutting pattern.

11. A biochip measuring system, comprising:
a biochip, comprising:
a substrate, for carrying bio-molecule droplet; and
a stamp marking area, for receiving or displaying a stamp for identifying whether the biochip is used; and
a biochip measuring apparatus, comprising:
a controller;
a driver circuit, electrically connected to the controller;
a driver interface, electrically connected to the driver circuit, and contacting with the biochip be measured;
a light, electrically connected to the controller, for timely providing a measuring light to the biochip;
a light detector electrically connected to the controller for detecting a light reaction after the light irradiates the biochip and generating a measuring result; and
a stamp marking unit, for marking the stamp on the stamp marking area of the biochip after the biochip measuring apparatus completes measurement of the biochip;
wherein the stamp marking unit marks the stamp with a plurality of electrical switches, and the stamp marked by the plurality of electrical switches comprises a plurality of fuses, and the stamp marking unit burns at least one corresponding fuse among the plurality of fuses with a large current and generates at least one corresponding open circuit with a predefined manner when a corresponding portion of the measurement of the biochip is completed, to mark the stamp.

12. The biochip measuring system of claim 11, wherein the plurality of fuses is a plurality of narrow traces.

13. The biochip measuring system of claim 11, wherein a stamp identification unit comprises a detecting circuit, for detecting open statuses of the plurality of fuses, to identify the stamp.

14. The biochip measuring system of claim 11, wherein the predefined manner is burning the at least one fuse corresponding to the portion of the measurement and not burning other fuses among the plurality of fuses not corresponding to the portion of the measurement when the corresponding portion of the measurement of the biochip is completed.

15. The biochip measuring system of claim 11, wherein all of the plurality of fuses are burnt when all of the measurement of the biochip is completed.

16. A biochip measuring system, comprising:
a biochip, comprising:
a substrate, for carrying bio-molecule droplet; and
a stamp marking area, for receiving or displaying a stamp for identifying whether the biochip is used; and
a biochip measuring apparatus, comprising:
a controller;
a driver circuit, electrically connected to the controller;
a driver interface, electrically connected to the driver circuit, and contacting with the biochip be measured;
a light, electrically connected to the controller, for timely providing a measuring light to the biochip;
a light detector, electrically connected to the controller, for detecting a light reaction after the light irradiates the biochip and generating a measuring result; and
a stamp marking unit, for marking the stamp on the stamp marking area of the biochip after the biochip measuring apparatus completes measurement of the biochip;
wherein the stamp marking unit marks the stamp with a color-changing of a color-changing material.

17. The biochip measuring system of claim 16, wherein a color-changing chemical in the stamp marking area changes to a specific color due to oxidation or humidity variations, to mark the stamp.

18. The biochip measuring system of claim 16, wherein a color-changing material in the stamp marking area changes to a specific color due to changes of one of electrical energy, light energy, or thermal energy, to mark the stamp.

19. The biochip measuring system of claim 16, wherein the biochip measuring apparatus further comprises a color detector, for detecting the specific color, to identify the stamp.

20. A biochip measuring apparatus, for measuring a biochip, comprising:
a driver circuit, electrically connected to a controller;
a driver interface, electrically connected to the driver circuit, and contacting with the biochip be measured;
a light, electrically connected to the controller, for timely providing a measuring light to the biochip;
a light detector, electrically connected to the controller, for detecting a light reaction after the light irradiates the biochip and generating a measuring result; and a stamp marking unit, for marking the stamp on the stamp marking area of the biochip after the biochip measuring apparatus completes measurement of the biochip;

wherein the stamp marking unit marks the stamp by adding a particular pattern for recognition with a surface processing.

21. The biochip measuring apparatus of claim 20, wherein the biochip measuring apparatus further comprises a stamp identification unit, for identifying whether the stamp is on the stamp marking area of the biochip, to decide whether the biochip measuring apparatus measures the biochip.

22. The biochip measuring apparatus of claim 21, wherein the biochip measuring apparatus does not measure the biochip when the stamp identification unit detects the stamp is on the stamp marking area of the biochip.

23. The biochip measuring apparatus of claim 22, wherein the biochip measuring apparatus further comprises a warning unit, for making or displaying a warning message when the stamp identification unit detects the stamp is on the stamp marking area of the biochip and does not measure the biochip.

24. The biochip measuring apparatus of claim 21, wherein the biochip measuring apparatus measures the biochip when the stamp identification unit detects the stamp is not on the stamp marking area of the biochip, and the stamp marking unit marks the stamp on the biochip after the biochip measuring apparatus completes measurement of the biochip.

25. The biochip measuring apparatus of claim 20, wherein the surface processing comprises an ink coating, a printing or an optical etching.

26. The biochip measuring apparatus of claim 25, wherein the stamp is a text pattern or an icon pattern.

27. The biochip measuring apparatus of claim 20, wherein biochip measuring apparatus is a flow cytometer.

28. A biochip measuring apparatus, for measuring a biochip, comprising:
a driver circuit, electrically connected to the controller;
a driver interface, electrically connected to the driver circuit, and contacting with the biochip be measured;
a light, electrically connected to the controller, for timely providing a measuring light to the biochip;
a light detector, electrically connected to the controller, for detecting a light reaction after the light irradiates the biochip and generating a measuring result; and
a stamp marking unit, for marking the stamp on the stamp marking area of the biochip after the biochip measuring apparatus completes measurement of the biochip;
wherein the stamp marking unit marks the stamp with a mechanical destroying manner.

29. The biochip measuring apparatus of claim 28, wherein the stamp is a hole drilling pattern or an edge cutting pattern.

30. A biochip measuring apparatus, for measuring a biochip, comprising:
a driver circuit, electrically connected to the controller;
a driver interface, electrically connected to the driver circuit, and contacting with the biochip be measured;
a light, electrically connected to the controller, for timely providing a measuring light to the biochip;
a light detector, electrically connected to the controller, for detecting a light reaction after the light irradiates the biochip and generating a measuring result; and
a stamp marking unit, for marking the stamp on the stamp marking area of the biochip after the biochip measuring apparatus completes measurement of the biochip;
wherein the stamp marking unit marks the stamp with a plurality of electrical switches, and the stamp marked by the plurality of electrical switches comprises a plurality of fuses, and the stamp marking unit burns at least one corresponding fuse among the plurality of fuses with a large current and generates at least one corresponding open circuit with a predefined manner when a corresponding portion of the measurement of the biochip is completed, to mark the stamp.

31. The biochip measuring apparatus of claim 30, wherein the plurality of fuses is a plurality of narrow traces.

32. The biochip measuring apparatus of claim 30, wherein a stamp identification unit comprises a detecting circuit, for detecting open statuses of the plurality of fuses, to identify the stamp.

33. The biochip measuring apparatus of claim 30, wherein the predefined manner is burning the at least one fuse corresponding to the portion of the measurement and not burning other fuses among the plurality of fuses not corresponding to the portion of the measurement when the corresponding portion of the measurement of the biochip is completed.

34. The biochip measuring apparatus of claim 30, wherein all of the plurality of fuses are burnt when all of the measurement of the biochip is completed.

35. A biochip measuring apparatus, for measuring a biochip, comprising:
a driver circuit, electrically connected to the controller;
a driver interface, electrically connected to the driver circuit, and contacting with the biochip be measured;
a light, electrically connected to the controller, for timely providing a measuring light to the biochip;
a light detector, electrically connected to the controller, for detecting a light reaction after the light irradiates the biochip and generating a measuring result; and
a stamp marking unit, for marking the stamp on the stamp marking area of the biochip after the biochip measuring apparatus completes measurement of the biochip;
wherein the stamp marking unit marks the stamp with a color-changing of a color-changing material.

36. The biochip measuring apparatus of claim 35, wherein a color-changing chemical in the stamp marking area changes to a specific color due to oxidation or humidity variations, to mark the stamp.

37. The biochip measuring apparatus of claim 35, wherein a color-changing material in the stamp marking area changes to a specific color due to changes of one of electrical energy, light energy, or thermal energy, to mark the stamp.

38. The biochip measuring apparatus of claim 35, wherein the biochip measuring apparatus further comprises a color detector, for detecting the specific color, to identify the stamp.

39. A biochip, comprising:
a substrate, for carrying bio-molecule droplet; and
a stamp marking area, located on the substrate, for receiving or displaying a stamp for identifying whether the biochip is used;
wherein, a biochip measuring apparatus marks the stamp on the stamp marking area of the biochip after completing measurement of the biochip;
wherein the stamp marking area comprises a plurality of fuses, and at least one corresponding fuse among the plurality of fuses is burnt with a large current to generate at least one corresponding open circuit with a predefined manner when a corresponding portion of the measurement of the biochip is completed, to mark the stamp.

40. The biochip of claim 39, wherein the biochip measuring apparatus identifies whether the stamp is on the stamp marking area of the biochip first, to decide whether the biochip measuring apparatus measures the biochip.

41. The biochip of claim 39, wherein the plurality of fuses is a plurality of narrow traces.

42. The biochip of claim 39, wherein the biochip measuring apparatus is a flow cytometer.

43. The biochip of claim 39, wherein the predefined manner is burning the at least one fuse corresponding to the portion of the measurement and not burning other fuses among the plurality of fuses not corresponding to the portion of the measurement when the corresponding portion of the measurement of the biochip is completed.

44. The biochip of claim 39, wherein all of the plurality of fuses are burnt when all of the measurement of the biochip is completed.

45. A biochip, comprising:
- a substrate, for carrying bio-molecule droplet; and
- a stamp marking area, located on the substrate, for receiving or displaying a stamp for identifying whether the biochip is used;
- wherein, a biochip measuring apparatus marks the stamp on the stamp marking area of the biochip after completes measurement of the biochip;
- wherein a color-changing chemical in the stamp marking area changes to a specific color due to oxidation or humidity variations, to mark the stamp.

* * * * *